United States Patent
Levieux

(10) Patent No.: US 8,790,404 B2
(45) Date of Patent: Jul. 29, 2014

(54) INTERVERTEBRAL DISK PROSTHESES

(75) Inventor: Jérôme Levieux, Bellevue (CH)

(73) Assignee: Spineart SA, Geneva (CH)

( * ) Notice: Subject to any disclaimer, the term of this patent is extended or adjusted under 35 U.S.C. 154(b) by 865 days.

(21) Appl. No.: 12/282,883

(22) PCT Filed: Mar. 13, 2007

(86) PCT No.: PCT/FR2007/000434
§ 371 (c)(1),
(2), (4) Date: Sep. 15, 2008

(87) PCT Pub. No.: WO2007/104860
PCT Pub. Date: Sep. 20, 2007

(65) Prior Publication Data
US 2009/0088856 A1  Apr. 2, 2009

(30) Foreign Application Priority Data
Mar. 14, 2006  (FR) ...................... 06 02226

(51) Int. Cl.
*A61F 2/44* (2006.01)
(52) U.S. Cl.
USPC ....................................... 623/17.14
(58) Field of Classification Search
USPC .......................................... 623/17.11–17.16
See application file for complete search history.

(56) References Cited

U.S. PATENT DOCUMENTS

| | | | | |
|---|---|---|---|---|
| 4,932,969 A * | 6/1990 | Frey et al. | .................. | 623/17.12 |
| 6,368,350 B1 * | 4/2002 | Erickson et al. | ........... | 623/17.14 |
| 6,582,466 B1 | 6/2003 | Gauchet | | |
| 7,250,060 B2 * | 7/2007 | Trieu | .......................... | 623/17.15 |
| 2004/0093082 A1 * | 5/2004 | Ferree | ......................... | 623/17.11 |
| 2004/0143334 A1 | 7/2004 | Ferree | | |
| 2004/0243238 A1 * | 12/2004 | Arnin et al. | ................. | 623/17.12 |
| 2004/0243240 A1 * | 12/2004 | Beaurain et al. | ........... | 623/17.14 |
| 2005/0131542 A1 * | 6/2005 | Benzel et al. | .............. | 623/17.13 |
| 2005/0165485 A1 | 7/2005 | Trieu | | |
| 2005/0187633 A1 * | 8/2005 | Ferree | ......................... | 623/17.15 |
| 2005/0197702 A1 * | 9/2005 | Coppes et al. | ............. | 623/17.12 |
| 2005/0246022 A1 * | 11/2005 | Zubok et al. | ................ | 623/17.11 |
| 2005/0251260 A1 * | 11/2005 | Gerber et al. | .............. | 623/17.13 |
| 2006/0020341 A1 * | 1/2006 | Schneid et al. | ............ | 623/17.14 |
| 2006/0041314 A1 * | 2/2006 | Millard | ....................... | 623/17.16 |
| 2006/0155377 A1 * | 7/2006 | Beaurain et al. | ........... | 623/17.15 |

(Continued)

FOREIGN PATENT DOCUMENTS

| | | |
|---|---|---|
| EP | 1 344 508 A1 | 3/2002 |
| FR | 2 775 587 A1 | 9/1999 |

(Continued)

*Primary Examiner* — Mary Hoffman
*Assistant Examiner* — Michelle C Eckman
(74) *Attorney, Agent, or Firm* — Young & Thompson

(57) ABSTRACT

Intervertebral disc prosthesis includes an upper plateau (16) with an outer surface (16a) bearing on an upper vertebra and with a surface (16b) directed towards the inside of the prosthesis, a lower plateau (18) with an outer surface (18a) bearing on a lower vertebra and with a surface (18b) directed towards the inside of the prosthesis, and a ball-type joint between the upper plateau and the lower plateau, having a bulged convex element (27), cooperating with a complementary recess of the bulged convex element (27) and coming into contact with the bulged convex element (27), the bulged convex element (27) including at least one slot (24, 25, 26, 28) that allows it to deform.

10 Claims, 3 Drawing Sheets

(56) References Cited

U.S. PATENT DOCUMENTS

2006/0190084 A1* 8/2006 Doubler et al. ............ 623/17.14
2006/0235526 A1* 10/2006 Lemaire ..................... 623/17.14
2008/0300688 A1* 12/2008 Cannon et al. ............. 623/17.16
2009/0018661 A1* 1/2009 Kim et al. .................. 623/17.16
2012/0116512 A1* 5/2012 Sournac et al. ............ 623/17.16

FOREIGN PATENT DOCUMENTS

| FR | 2 787 014 A1 | 6/2000 |
| FR | 2 799 116 A1 | 4/2001 |
| WO | 03099172 A1 | 12/2003 |
| WO | 2004/016217 A2 | 2/2004 |

* cited by examiner

INTERVERTEBRAL DISK PROSTHESES

BACKGROUND OF THE INVENTION (1) Field of the Invention

The present invention relates to intervertebral disks prostheses.

Degenerative processes due to a trauma, diseases or aging often lead to the replacement of an intervertebral disk.

These degenerative processes can involve a change in the natural space between two vertebrae. The contraction of this natural space can cause a pressure which acts on certain nerves, and as a result pain can occur.

A disk prosthesis can be used to maintain the natural space between two vertebrae.

It must also allow the vertebrae to move in relation to each other following a natural movement. In particular it must allow an axial rotation movement which corresponds in part to the rotational movement of the trunk or neck of the human body in the cervical region, an anteroposterior movement which corresponds to a movement bending or extending the upper part of the body or head in the cervical region, and a lateral movement which corresponds to a tilting of the upper part of the body or the neck in the cervical region.

The upper and lower plateaux of a disk prosthesis bear on the vertebrae and over time become fixed thereto as a result of surface treatments and the roughnesses with which they are generally provided.

(2) Description of Related Art

EP-A1-1 344 508 describes an intervertebral disk prosthesis comprising an upper plateau, a lower plateau having a bearing surface, an intermediate part comprising a lower surface and an upper surface having a spherical part, the upper plateau having an impression complementing the spherical part and coming into contact with the spherical part so as to define a ball-socket joint between the upper plateau and the intermediate part, the lower surface of the intermediate part coming into contact with the bearing surface.

The intermediate part can move forwards and backwards on the bearing surface of the lower plateau.

However, this type of prosthesis does not provide the desired comfort and robustness, in particular during violent impacts.

WO2004/016217 describes intervertebral disks prostheses. A wide variety of configurations is proposed. In one of these, there are provided a lower plateau, an upper plateau and an intermediate part comprising an upper convex surface to cooperate with a cavity created in the upper plateau. The intermediate part comprises long narrow horizontal notches.

However, in order to give an adequate shock absorption, this type of prosthesis would necessitate very deep notches creating fatigue rupture cracks which would considerably weaken the prosthesis and in particular would not provide the desired robustness, particularly during violent impacts or rotation.

BRIEF SUMMARY OF THE INVENTION

An aim of the present invention is in particular to overcome these drawbacks.

For this reason, the subject of the present application is an intervertebral disk prosthesis comprising an upper plateau having an external surface bearing on an upper vertebra and a surface directed towards the inside of the prosthesis, a lower plateau having an external surface bearing on a lower vertebra and a surface directed towards the inside of the prosthesis and a ball-socket joint between the upper plateau and the lower plateau, comprising a convex domed part, preferably spherical, cooperating with an impression complementing the convex domed part and coming into contact with said convex domed part, said convex domed part comprising at least one lumen allowing it to deform during sudden or vibratory movements in everyday life, in particular in the case of vertical impact.

Deformation of the domed part during sudden or vibratory movements in everyday life (impact, jump, accident, fall, violent effort, stressful sport (skiing, horse riding, etc.)) will consist essentially in a flattening of said convex domed part, i.e. a reduction in its height. Preferably, no deformation of the domed part will take place during the normal movements of daily life such as walking.

In preferred conditions of implementation of the invention, an above-mentioned intervertebral disk prosthesis is made in three parts.

The part of the prosthesis comprising the convex domed part is then an intermediate piece inserted between the two plateaux.

For example, the assembly can comprised a lower plateau having an external surface bearing on a lower vertebra and a surface directed towards the inside of the prosthesis acting as a bearing surface for an intermediate part comprising a lower surface and a upper surface having a domed part, preferably spherical, and an upper plateau having an external surface bearing on a upper vertebra and a surface directed towards the inside of the prosthesis having an impression complementing the domed part and coming into contact with said domed part so as to define a ball-socket joint between the upper plateau and the intermediate part.

The intermediate part can also correspond to the convex domed part only, which will then be inserted in a recess provided in the lower plateau. It will then have the general form of a short cylinder topped by a domed cap, in particular spherical.

In other preferred conditions of implementation of the invention, an above-mentioned intervertebral disk prosthesis is made in two parts.

For example, the assembly can comprise a lower plateau which has an external surface bearing on a lower vertebra and a surface directed towards the inside of the prosthesis having a domed part, and an upper plateau having an impression complementing the domed part and coming into contact with said domed part so as to define a ball-socket joint between the upper plateau and the lower plateau, the two inwardly-directed surfaces coming into contact with each other.

The recess provided in the convex domed part comprises at least one lumen. This can be of any shape, preferably regular and comprising at least one axis of symmetry, for example cubic or parallelepipedic, spherical, oblong etc. It is noted that, within the framework of the present invention a lumen is a closed cavity, which distinguishes it from a notch which is open to the outside.

There can be one or more lumina, sometimes also called recesses below. These are preferably inserted regularly in relation to the axes of symmetry of the domed part. However, an asymmetrical insertion will be preferred, for example, to carry out a correction or confer a particular effect.

The lumen or lumina can be in the form of horizontal slit(s), alternated or stacked or oblique in the case of plurality of slits, joined or spaced holes, in particular parallelepipedic in shape or preferably circular, aligned or not, or holes linked by a longitudinal slit, seen in cross section.

The nature of the material used to make the part having a domed part governs the structure and the size of the recess(es).

The shape and the number of recesses will be chosen according to the desired shock absorption. Assuming an identical material is used, the larger the dimensions of the recess, the more deformable will be the convex domed part. Similarly, the larger the number and/or volume of the recesses, the more deformable will be said domed part.

A person skilled in the art can, by means of a few simple experiments, determine the shape, the size of the lumina and the material used to achieve the desired deformability.

The recess is provided inside the domed part without emerging on the outside thereof.

The recess(es) can have a convex shape, for example in the form of a cap, or else a substantially spherical or oblong shape.

In the case of an above-mentioned intervertebral disk prosthesis made in three parts, a prosthesis is preferred of which:
- the lower surface of the intermediate part has a concave part opening to the outside,
- the lower surface of the intermediate part has a concave part opening to the outside and comprises a flat part around the concave part and the surface ratio between the concave part and the flat part is for example comprised between 1/5 and 9/10, advantageously comprised between 1/4 and 9/10, particularly comprised between 1/4 and 4/5, in particular comprised between 1/4 and 3/4, quite particularly comprised between 1/3 and 3/4.
- the bearing surface has a concave-shaped part, in this case the lumen is constituted by this concavity, closed by the intermediate part as shown below in FIG. 1.
- the bearing surface comprises a flat part around the concave part and the surface ratio between the concave part and the flat part is for example comprised between 1/5 and 9/10, advantageously comprised between 1/4 and 9/10, in particular comprised between 1/4 and 4/5, particularly comprised between 1/4 and 3/4, quite particularly comprised between 1/3 and 3/4,
- the lower plateau comprises edges delimiting the bearing surface.

As the cavity constituted by the concave part can be very thin (a few tenths of a millimeter), a cavity without a flat ring around the concave part will function in the same way; in fact, this ring will form when a load is applied. In this case the surface of the ring will not be completely flat. This is the case for example with a spherical-shaped recess with a large radius of curvature.

A person skilled in the art will readily understand that if for example the lower surface of the intermediate part has a concave part opening to the outside and bears on a flat surface of the lower plateau directed towards the inside of the prosthesis, an identical shock absorption effect can be achieved (FIG. 2). Similarly, by providing a concavity in the surface of the lower plateau directed towards the inside of the prosthesis, whereas the intermediate part has no recess, an identical shock absorption effect can be achieved (FIG. 1). Such equivalent variant embodiments are included within the scope of the invention. It will also readily be understood that the adjectives "lower" and "upper" have a relative meaning, as a prosthesis of the invention can be implanted in one direction or the other. Thus, in the case of an above-mentioned intervertebral disk prosthesis made in two parts, the "lower" plateau having a domed part can be found towards the feet or alternatively towards the head of the individual in whom it is implanted.

A domed spherical part will have for example an external diameter of 0.5 to 10 cm, preferably 1 to 8 cm, in particular 1.5 to 7 cm, quite particularly 2 to 5 cm, in the case of a lumbar prosthesis, whether made in 2 or 3 parts (or more).

A domed spherical part will have for example an external diameter of 0.3 to 8 cm, preferably 0.5 to 7 cm, in particular 0.8 to 5 cm, quite particularly 1 to 3 cm, in the case of a cervical prosthesis, whether made in 2 or 3 parts (or more).

The different parts can be made of different materials or from the same material. Preferably the part comprising a convex domed part, in particular the intermediate part in an above-mentioned intervertebral disk prosthesis comprising three parts, is made of thermoplastic resin or of pyrocarbon such as that marketed by the company BioProfile (Grenoble France) under the name Pyc®. The thermoplastic resin is for example polyethylene with a high molecular weight and preferably polyether ether ketone (PEEK), reinforced with glass or carbon fibres but preferably pure.

In the case of an above-mentioned intervertebral disk prosthesis made in two parts,
- the upper plateau can be made of a material of the chrome-cobalt or titanium or stainless steel type. The upper plateau can also be made of polyether ether ketone (PEEK), preferably having a surface coating of titanium on its upper face. The upper plateau can also be made of material of the chrome-cobalt or titanium or stainless steel type and have a hardening surface treatment (in particular of Diamolith® type, marketed by the company IonBond or Innovative Coatings Company—Le Mée sur Seine, FRANCE) or a pyrocarbon insert in order to improve its friction and wear properties.
- the intermediate part can be made of a plastic material of the high-density polyethylene type, having very good slip characteristics,
- the intermediate part can also be made of a material such as polyether ether ketone (PEEK) or pyrocarbon which has a Young's modulus of approximately 24 Mpa which gives it a degree of elasticity in the case of impacts.
- the lower plateau can be made of a material of the chrome-cobalt or titanium or stainless steel type. The lower plateau can also be made of polyether ether ketone (PEEK), having a surface coating of titanium on its upper face. The upper plateau can also be made of material of the chrome-cobalt or titanium or stainless steel type and have a hardening surface treatment (in particular of the Diamolith® type, marketed by the company IonBond) or a pyrocarbon insert in order to improve its friction and wear properties.

In preferred conditions of implementation of the invention, an above intervertebral disk prosthesis is made in three parts and the lower and upper plateaux have a hardening surface coating on their internal face. In other preferred embodiments of the invention, the lower and upper plateaux have a pyrocarbon insert on their internal face.

In the case of an above-mentioned intervertebral disk prosthesis made in three parts,
- the upper plateau and the lower plateau can be made of a material of the chrome-cobalt or titanium or stainless steel type or be made of material of the chrome-cobalt or titanium or stainless steel type and have a hardening surface treatment (in particular of the Diamolith® type, marketed by the company IonBond) or a pyrocarbon insert in order to improve its friction and wear properties, or be made of PEEK.

The prostheses which are the subject of the present invention have very useful properties and qualities.

The recess(es) provided in the convex domed part make it possible, by deformation of the domed part, to absorb the impacts to which the prosthesis is subjected.

They thus offer a comfort in use and an improved robustness compared with the prostheses of the prior art. In particular, they make it possible to absorb impacts by deformation of the material of the domed part, and thus to prevent the prosthesis from working loose.

These properties are illustrated below in the experimental part. They justify the use of the above-described prostheses in the replacement of an intervertebral disk subject to degenerative processes following a trauma, diseases or aging.

To this end, they can be implanted in an individual such that the convexity is directed downwards or preferably upwards.

Thus a further subject of the present application is a method for replacing an intervertebral disk subject for example to degenerative processes following a trauma, diseases or aging, in which at least one above-mentioned prosthesis is implanted between two adjacent vertebrae.

Advantageously, the plateau having an impression complementing the domed part is implanted above the one comprising the domed part.

The preferred conditions of implementation of the above-described intervertebral prostheses also apply to the other above-mentioned subjects of the invention, in particular to the methods for replacement of an intervertebral disk.

BRIEF DESCRIPTION OF THE SEVERAL VIEWS OF THE DRAWINGS

The invention will be better understood with reference to the attached drawings in which.

DETAILED DESCRIPTION OF THE INVENTION

The same references in different figures denote identical or similar parts.

Figure 5:
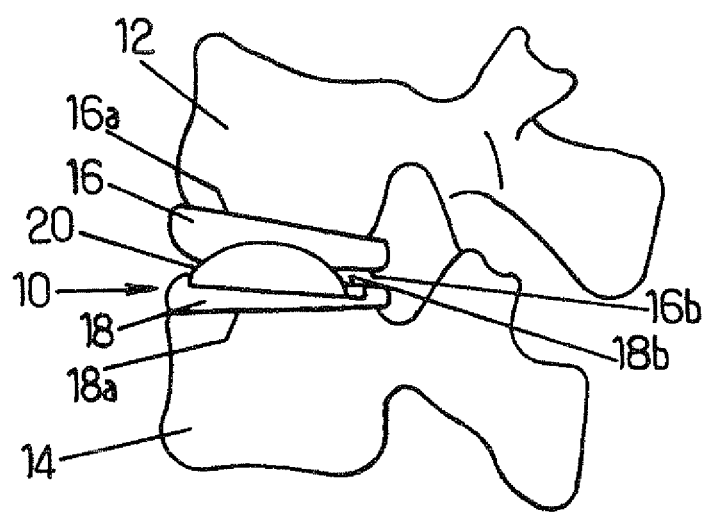
FIG. 5 represents a side view of a disk prosthesis in three parts positioned between two vertebrae.

The disk prosthesis 10 is intended to be positioned between two vertebrae of a vertebral column 12, 14. For example FIG. 5 illustrates a profile view of two vertebrae 12, 14 of a vertebral column between which is positioned a prosthesis 10 according to the invention.

The disk prosthesis 10 comprises an upper plateau 16 and a lower plateau 18 each having an external face 16a, 18a oriented respectively towards an upper vertebra and a lower vertebra. Reliefs, for example in a saw-tooth pattern, not shown, which allow the plateaux 16, 18 to be anchored in the vertebrae are arranged on each of the external faces 16a, 18a.

The upper 16 and lower 18 plateaux also each comprise an internal surface 16b, 18b. The internal surfaces extend laterally along a first anteroposterior axis and extend longitudinally along a second axis perpendicular to the first axis, facing each other, and they are in contact with an intermediate part 20.

The intermediate part 20 comprises an upper surface having a spherical convex domed part 27. It also comprises a lower face bearing on the internal surface 18b (which will hereinafter be called "bearing surface 18b") of the lower plateau 18. The spherical part 27 of the upper face is in contact with the internal surface 16b of the upper plateau 16. The domed part 27 makes it possible to obtain a "ball-socket" type joint to permit movement of the intermediate part 20 in all directions with respect to the upper plateau 16, offering a greater flexibility.

The intermediate part 20 is mounted mobile on the bearing surface 18b of the lower plateau 18. Moreover, the lower plateau comprises a edge 19 delimiting the bearing surface 18b.

The ball-socket joint between the upper plateau 16 fixed over time to the upper vertebra 12 and the intermediate part 20 itself linked to the lower vertebra 14 by the lower plateau 18, makes it possible to reproduce the bending or extension movements and the tilting movements between two vertebrae 12, 14 of a vertebral column.

Figure 1:
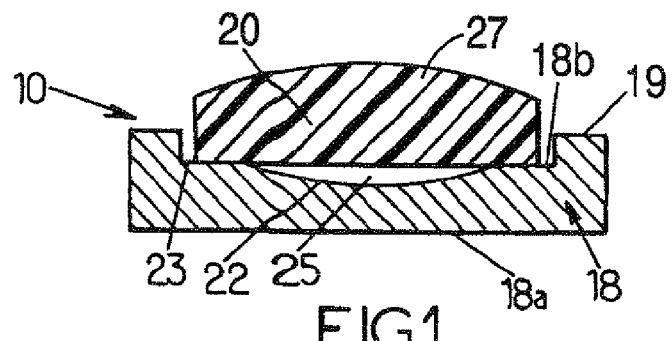
FIG. 1 represents a diagrammatic side view of a part of a disk prosthesis according to a first embodiment in three parts (two shown)

As shown in FIG. 1, the lower plateau 18 comprises, on its bearing face 18b, a concave-shaped part 22 and a flat part 23, the whole facing the lower part of the intermediate part 20, in order to form a recess 25. This concave part 22 has a surface dimension smaller than that of the lower surface of the intermediate part 20, such that the intermediate part 20 can move on the flat part 23 of the bearing surface 18b of the lower plateau 18. The surface ratio between the concave part and the lower surface of the intermediate part shown here is approximately 3/4. In this embodiment moreover, the concave part 22 creates the lumen (25) according to the invention.

In a variant, the cavity constituted by the concave part is very thin (a few tenths of a millimeter). The lower plateau 18 does not have a flat part 23. A ring corresponding to the above flat part 23 will form naturally on the circumference of the lower plateau as soon as a load is applied. In this case the surface of the ring will not be completely flat. This is the case for example with a spherical-shaped recess having a large radius of curvature (5 or 25 cm radius for example according to whether it is a cervical or lumbar device).

When the disk prosthesis is subjected to impacts, directed substantially in a vertical direction, such as falls onto the buttocks or during a jump, a force tends to bring the upper plateau 16 closer to the lower plateau 18, and the intermediate part 20 is consequently compressed between the two plateaux. The intermediate part 20 deforms under the action of the force exerted by the spinal column during the impact and tends to fill the empty space of the recess 25, the impact then being absorbed by the deformation of the intermediate part 20. The risks of vertebral fractures or working loose are then reduced.

Figure 2:
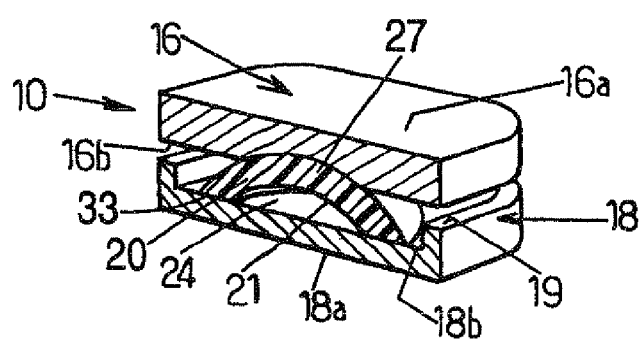
FIGS. 2 and 3 represent a perspective view sectioned along a vertical plane of a disk prosthesis according to a second and a third embodiment in three parts.
Figure 3:
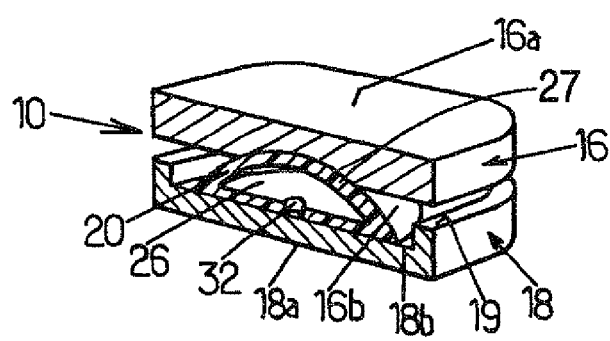
Figure 4:
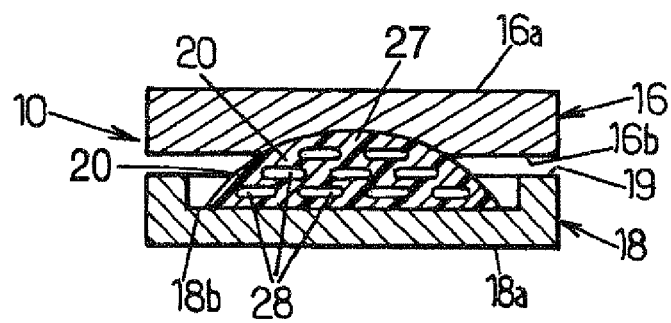
FIG. 4 represents a sectional side view of a disk prosthesis according to a fourth embodiment in three parts.

According to other embodiments shown in FIGS. 2 to 4, the recess has been provided on the intermediate part.

In FIG. 2, the recess 24 is provided on the lower face of the intermediate part 20. For this, the lower surface of the intermediate part has a concave-shaped part 21 facing the flat bearing surface 18b. This concave lumen is plugged by the lower plateau 18. Thus when a force is applied to the prosthesis, the intermediate part 20 is deformed and tends to occupy the space formed between the concave part 21 and the bearing surface 18b. The lower surface of the intermediate part also comprises a flat part 33 around the concave part 21, and the surface ratio between the concave part 21 and the flat part 33 shown here is approximately 1.5. The flat part is in contact with the bearing surface 18*b* of the lower plateau 18 and thus ensures the slipping movement of the intermediate part 20 on the bearing surface 18*b*. The recess opens to the outside of the domed part, allowing the contents of the recess 24 to be expelled when the intermediate part 20 is deformed, regardless of the plugging by the lower plateau 18.

In FIG. 3, the recess 26 is provided as an inclusion in the spherical part 27 of the intermediate part 20 and forms a cavity. The intermediate part 20 also comprises a passage 32 allowing the cavity 26 to communicate with the outside of the intermediate part 20. This passage 32, although plugged by the lower plateau 18, nevertheless allows the contents of the cavity to be expelled when the intermediate part 20 is deformed, and as a result allows a better shock absorption by increasing the deformation capacities of the intermediate part and by preventing rebounds when the intermediate part returns to its initial shape. Also in this variant, the recess opens to the outside of the domed part.

In FIG. 4, the domed part 27 of the intermediate part 20 comprises several lumina or recesses 28, oblong-shaped in section and arranged approximately parallel to a direction perpendicular to the vertical axis Z, which makes it possible to more easily deform the intermediate part 20 under the action of a vertical force. These recesses are not linked to an air expulsion passage such as described previously, and do not open to the outside thereof.

Figure 6:
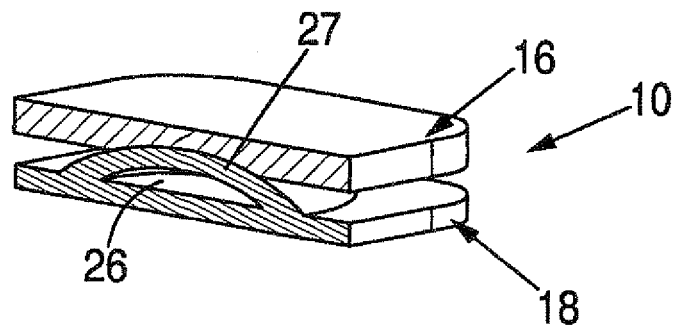
FIGS. 6, 7 and 8 represent a sectional side view of a disk prosthesis according to an embodiment in two parts.
Figure 7:
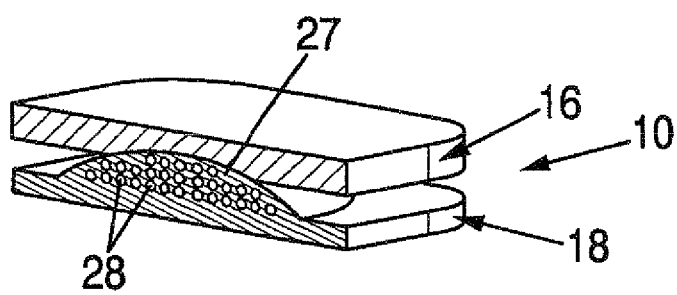
Figure 8:
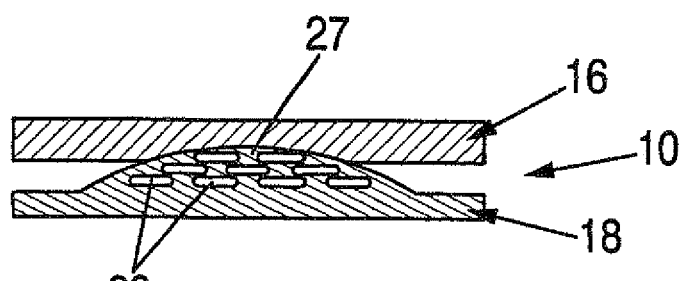

FIGS. 6, 7, 8 show a disk prosthesis 10 comprising an upper plateau 16 and a lower plateau 18, the latter integrally comprising a spherical convex domed part 27, cooperating with a complementary impression arranged in the upper plateau 16.

The invention claimed is:

1. An intervertebral disk prosthesis, comprising:
an upper plateau (16) having i) an upper external surface (16*a*) capable of bearing on an upper vertebra, ii) a lower surface (16*b*) directed downwardly, and iii) a upwardly convex depression within the lower surface (16*b*);
a lower plateau (18) having
i) a lower external surface (18*a*) capable of bearing on a lower vertebra,
ii) an upper bearing surface (18*b*) directed upwardly towards the lower surface (16*b*) of the upper plateau (16), the upper bearing surface (18*b*) being comprised of an upwardly concave-shaped surface part (22) surrounded by a flat part (23), and
iii) an upwardly extending edge (19) delimiting the flat part (23) of the upper bearing surface (18*b*) of the lower plateau (18), a region open to an environment outside of the intervertebral disk prosthesis being present between the lower surface (16) of the upper plateau (16) and the top edge surface of the upwardly extending edge (19) such that a part of the flat part (23) delimited by the upwardly extending edge (19) is open to the environment outside of the intervertebral disk prosthesis; and
an intermediate part (20) comprising an upper surface defined by a spherical upwardly convex domed part (27) and a lower surface,
the intermediate part (20) being located between the lower surface (16*b*) of the upper plateau and the upper bearing surface (18*b*) of the lower plateau,
the upwardly convex domed part (27) being in movable contact with the upwardly convex depression within the lower surface (16*b*) of the upper plateau (16),
the lower surface of the intermediate part (20) being carried by direct contact with the flat part (23) of the upper bearing surface (18*b*) of the lower plateau (18),
the intermediate part (20) being laterally movable on an area of the flat part (23) of the upper bearing surface (18*b*) of the lower plateau (18) delimited by the upwardly extending edge (19); and
a lumen (25) defined by the upwardly concave-shaped surface part (22) of the upper bearing surface (18*b*) of the lower plateau (18) and a portion of the lower surface of the intermediate part (20),
wherein upon a vertical impact on the upwardly convex domed part (27) of the intermediate part (20) during sudden or vibratory movements in everyday life, elasticity of the intermediate part (20) allows deformation of the upwardly convex domed part (27) of the intermediate part (20) to at least partial fill the lumen; and
wherein the flat part (23) of the upper bearing surface (18*b*) of the lower plateau (18) is located around the upwardly concave-shaped surface part (22) of the upper bearing surface (18*b*) of the lower plateau (18), and a surface ratio between the upwardly concave-shaped concave part (22) and the flat part (23) of the upper bearing surface (18*b*) is in a range between 1/4 and 3/4.

2. The intervertebral disk prosthesis according to claim 1, wherein the upwardly convex domed part is made of polyether ether ketone.

3. The intervertebral disk prosthesis according to claim 1, further comprising a hardening surface coating on each of the lower surface (16*b*) of the upper plateau (16) and the upper bearing surface (18*b*) of the lower plateau (18).

4. The intervertebral disk prosthesis according to claim 1, wherein the lower and upper plateaus (16, 18) are made of polyether ether ketone.

5. The intervertebral disk prosthesis according to claim 1, wherein,
the intermediate part is made of a material with a Young's modulus of approximately 24 Mpa.

6. An intervertebral disk prosthesis, comprising:
an upper plateau (16) having i) an upper external surface (16*a*) capable of bearing on an upper vertebra, ii) a lower surface (16*b*) directed downwardly, and iii) a upwardly convex depression within the lower surface (16*b*);
a lower plateau (18) having
i) a lower external surface (18*a*) capable of bearing on a lower vertebra,
ii) an upper bearing surface (18*b*) directed upwardly towards the lower surface (16*b*) of the upper plateau (16), the upper bearing surface (18*b*) being comprised of an upwardly concave-shaped surface part (22) surrounded by a flat part (23), wherein the flat part (23) of the upper bearing surface (18*b*) of the lower plateau (18) is located around the upwardly concave-shaped surface part (22) of the upper bearing surface (18*b*) of the lower plateau (18), and
iii) an upwardly extending edge (19) delimiting the flat part (23) of the upper bearing surface (18*b*) of the lower plateau (18), a region open to an environment outside of the intervertebral disk prosthesis being present between the lower surface (16) of the upper plateau (16) and the top edge surface of the upwardly extending edge (19) such that a part of the flat part (23) delimited by the upwardly extending edge (19) is open to the environment outside of the intervertebral disk prosthesis; and
an intermediate part (20) comprising an upper surface defined by a spherical upwardly convex domed part (27) and a lower surface,
the intermediate part (20) being located between the lower surface (16*b*) of the upper plateau and the upper bearing surface (18*b*) of the lower plateau, the upwardly convex domed part (27) being in movable contact with the upwardly convex depression within the lower surface (16b) of the upper plateau (16), the lower surface of the intermediate part (20) being carried by direct contact with the flat part (23) of the upper bearing surface (18b) of the lower plateau (18), the intermediate part (20) being laterally movable on an area of the flat part (23) of the upper bearing surface (18b) of the lower plateau (18) delimited by the upwardly extending edge (19); and a lumen (25) defined by the upwardly concave-shaped surface part (22) of the upper bearing surface (18b) of the lower plateau (18) and a portion of the lower surface of the intermediate part (20), wherein upon a vertical impact on the upwardly convex domed part (27) of the intermediate part (20) during sudden or vibratory movements in everyday life, elasticity of the intermediate part (20) allows deformation of the upwardly convex domed part (27) of the intermediate part (20) to cause at least partial fill the lumen, wherein an outside perimeter of the intermediate part (20) bears on the flat part (23) of the upper bearing surface (18b) of the lower plateau (18), and wherein the portion of the lower surface of the intermediate part (20) defines a downwardly concave surface (21), and the lumen (25) is defined by a cavity (25) between the downwardly concave surface (21) of the intermediate part (20) and the upwardly concave-shaped surface part (22) of the upper bearing surface (18b) of the lower plateau (18).

7. The intervertebral disk prosthesis according to claim 6, wherein,
the intermediate part is made of a material with a Young's modulus of approximately 24 Mpa.

8. The intervertebral disk prosthesis according to claim 6, wherein the upwardly convex domed part is made of polyether ether ketone.

9. The intervertebral disk prosthesis according to claim 6, further comprising a hardening surface coating on each of the lower surface (16b) of the upper plateau (16) and the upper bearing surface (18b) of the lower plateau (18).

10. The intervertebral disk prosthesis according to claim 6, wherein the lower and upper plateaus (16, 18) are made of polyether ether ketone.

* * * * *